(12) United States Patent
Niklason et al.

(10) Patent No.: US 7,498,332 B2
(45) Date of Patent: Mar. 3, 2009

(54) THERAPY FOR CEREBRAL VASOSPASM

(75) Inventors: Laura E. Niklason, Hillsborough, NC (US); Andy McKee, Durham, NC (US); Cecil Borel, Chapel Hill, NC (US)

(73) Assignee: Duke University, Durham, NC (US)

( * ) Notice: Subject to any disclaimer, the term of this patent is extended or adjusted under 35 U.S.C. 154(b) by 187 days.

(21) Appl. No.: 10/074,250

(22) Filed: Feb. 14, 2002

(65) Prior Publication Data

US 2002/0160001 A1    Oct. 31, 2002

Related U.S. Application Data

(60) Provisional application No. 60/268,368, filed on Feb. 14, 2001.

(51) Int. Cl.
*A61K 31/497* (2006.01)
*C07D 471/04* (2006.01)
*C07D 471/22* (2006.01)
*C07D 487/04* (2006.01)

(52) U.S. Cl. .................. 514/252.11; 514/257

(58) Field of Classification Search ............ 514/252.02, 514/247, 249, 252.01, 252.11, 257
See application file for complete search history.

(56) References Cited

U.S. PATENT DOCUMENTS

| | | | | |
|---|---|---|---|---|
| 4,792,564 | A | * | 12/1988 | Harder et al. ................ 514/355 |
| 4,954,526 | A | * | 9/1990 | Keefer ........................ 514/611 |
| 5,527,778 | A | * | 6/1996 | Black ......................... 514/15 |
| 5,703,240 | A | | 12/1997 | Armour et al. |
| 5,994,350 | A | | 11/1999 | Foulon et al. |
| 5,998,468 | A | | 12/1999 | Cheng et al. |
| 6,379,691 | B1 | * | 4/2002 | Tedeschi et al. ............. 424/423 |
| 2002/0103454 | A1 | * | 8/2002 | Sackner et al. ............... 604/19 |

OTHER PUBLICATIONS

Hardman et al. "Goodman & Gilman's the Pharmacological Basis of Therapeutics" (9th ed, 1996) p. 51 and 57-58.*

* cited by examiner

*Primary Examiner*—Yong S Chong
(74) *Attorney, Agent, or Firm*—Nixon & Vanderhye P.C.

(57) ABSTRACT

The present invention relates to a method of treating or preventing cerebral vasospasm that accompanies sub-arachnoid hemorrhage.

2 Claims, 4 Drawing Sheets

THERAPY FOR CEREBRAL VASOSPASM

This is a continuation of Provisional Application No. 60/268,368 filed Feb. 14, 2001, the entire content of which is incorporated by reference.

TECHNICAL FIELD

The present invention relates, in general, to cerebral vasospasm and, in particular, to a method of treating or preventing cerebral vasospasm that accompanies subarachnoid hemorrhage (SAH).

BACKGROUND

Subarachnoid hemorrhage (SAH), resulting from intracerebral bleeding or from trauma, is a serious neurologic event. Frequent complications of SAH include cerebral infarction (stroke), cerebral edema with increased intracranial pressure, and death.

If a patient survives the initial insult of SAH, a further complication is that of cerebral vasospasm. Cerebral vasospasm is a syndrome that accompanies SAH and generally has peak clinical manifestations at 7-10 days following SAH. The syndrome is characterized by diffuse narrowing of cerebral arteries in the general region of the hemorrhage. Clinically, this arterial narrowing is correlated with the amount of blood that is present in the subarachnoid space. The arterial narrowing can become sufficiently severe that blood flow to previously undamaged brain is compromised, resulting in risk of subsequent stroke without adequate treatment.

Current treatment for vasospasm includes increasing systemic blood pressure and expanding the intravascular space, both of which are correlated clinically with improving symptoms of cerebral ischemia in vasospasm. This therapy necessitates an intensive care unit setting, is not universally successful, and can lead to complications in some patients.

Despite several decades of research, no clear etiology for vasospasm has been elucidated. Multiple general approaches have been taken, including investigation of vasoconstrictors, cytokines, and other pro-inflammatory modulators. None of these putative agents, however, has emerged as clearly causative in the syndrome of vasospasm.

Histologic analyses of cerebral vessels suffering from vasospasm has revealed evidence of vascular cell and adventitial cell proliferation at times of peak arterial narrowing. Vascular cell proliferation is often attributable to locally high concentrations of relevant mitogenic agents, such as growth factors. Intriguingly, blood that is outside the vascular space, such as blood in the subarachnoid space, spontaneously forms clots with concomitant platelet activation. Platelets are known to be repositories of several growth factors, including platelet-derived growth factors, that are potent mitogens for cells in the vascular wall.

The present invention results from the realization that the narrowing of cerebral arteries that is characteristic of cerebral vasospasm is in fact due to proliferation of cells in the vascular wall and/or accumulation of extracellular matrix under the influence of growth factors.

The extracellular matrix contains cross-linked collagen and elastin fibers. Collagen and elastin fibers in the extracellular matrix of blood vessels bear the tensile load in response to pressure from blood flow within the blood vessel. After their synthesis, collagen molecules are processed in the Golgi and endoplasmic recticulum. 4-Prolyl hydroxylase (PH) is the enzyme responsible for hydroxylating residues in collagen molecules (Kivirikko et al, Matrix Biology 16:357 (1998)). This modification permits collagen molecules to associate strongly in small helical fibers. Following production of helically-wound collagen fibers, collagen is excreted from the cell into the extracellular space, where it can be strengthened by spontaneously forming larger fibers ("fibrils") and by being cross-linked. Lysyl oxidase (LO) is the enzyme primarily responsible for cross-linking collagen and elastin fibers once these molecules have been secreted into the extracellular space. (Rucker et al, Am. J. Clin. Nutr. 67(suppl.):9965 (1998).) Collagen fibrils are substantially strengthened with the addition of cross-links between and within fibers that restrict movement of the fibers under tension.

The present invention provides a method of treating or preventing cerebral vasospasm by inhibiting vascular proliferation and/or extracellular matrix synthesis, secretion or strengthening (e.g., collagen fiber formation and self-assembly, as well as molecular cross-linking).

SUMMARY OF THE INVENTION

The present invention relates to a method of preventing or treating narrowing of cerebral arteries ("cerebral vasospasm") that accompanies SAH. The method comprises administering to a patient in need of such prevention or treatment an agent that inhibits vascular cell proliferation and/or extracellular matrix synthesis, secretion or strengthening.

Objects and advantages of the present invention will be clear from the description that follows.

BRIEF DESCRIPTION OF THE DRAWINGS

FIGS. 2A and 2B, immunostaining for proliferating cell nuclear antigen (PCNA). Marked increases in perivascular cellular proliferation were observed in SAH (FIG. 2B) versus sham mice (FIG. 2A), at all time points examined. While many PCNA-positive smooth muscle cell nuclei were noted within vascular media of the ACA and other cerebral arteries, the majority of positive nuclei were fibroblasts located in the adventitia and connective tissue surrounding cerebral vessels (arrowheads, FIG. 2B). FIGS. 2C and 2D, PDGF-AB/-BB immunostaining. There was extensive protein deposition of PDGF in the areas of thrombus formation in SAH mice (FIG. 2D), while PDGF-AB and -BB were essentially absent in sham mice (FIG. 2C). Thus, extensive smooth muscle and fibroblast proliferation was observed following SAH, and this cellular replication was correlated with evidence of PDGF protein near the sites of injury.

FIGS. 4A-4D, Proliferating cell nuclear antigen immunostaining (PCNA). Low levels of cellular proliferation (PCNA staining) were observed in time-zero control segments (group 1; FIG. 4A). Vessel segments that had been cultured in growth medium alone for 7 d (group 2) served as a culture control, and also showed low levels of vessel wall cellular proliferation (FIG. 4B). In contrast, segments exposed to coagulated human blood (group 3) displayed highly proliferative areas in the vessel wall, most frequently in the adventitia (circled area, FIG. 4C). This proliferation appeared to be blocked by premixing the human blood prior to coagulation with inhibiting concentrations of anti-PDGF-AB and anti-PDGF-BB antibodies (Group 4; FIG. 4D). These results indicate that localized thrombus can stimulate vessel wall proliferation in cerebral arteries, and that anti-proliferative agents can halt this thrombus-associated proliferation. These results are consistent with data obtained from the murine SAH model (see EXAMPLE II), and show that this phenomenon can be generalizable across species. 200× original magnification.

DETAILED DESCRIPTION OF THE INVENTION

Figure 1:
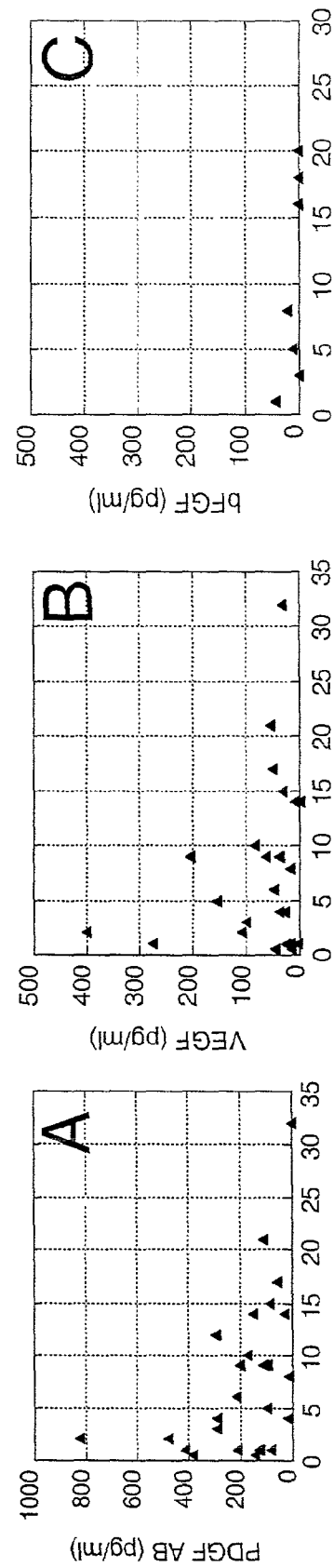
FIGS. 1A-1C. Temporal behavior of growth factor levels in the CSF of SAH patients. PDGF-AB (FIG. 1A) and VEGF (FIG. 1B) levels in SAH patients' CSF showed high concentrations during the first several days, followed by a gradual decay. PDGF-AB and VEGF levels began to approach control levels 3 weeks after SAH. In contrast, b-FGF (FIG. 1C), a growth factor that is not secreted by activated platelets and hence served as a negative control, was not substantially elevated in SAH or non-SAH patients SAH patients: 3.9±10.2 pg/ml; Non-SAH patients: 3.5±3.8 pg/ml; Normal Controls: 0±0.1 pg/ml). These results indicate increased levels vascular mitogens PDGF-AB and VEGF in the-CSF of SAH patients.

The present invention relates to a method of preventing or treating narrowing of cerebral arteries that accompanies SAH. The method comprises administering to a patient in need of such prevention or treatment an agent that inhibits vascular cell proliferation and/or extracellular matrix synthesis, secretion or strengthening.

Agents suitable for use in the present invention include compounds that inhibit mitogens of cells of the vascular wall, including smooth muscle cells and fibroblasts and pericytes. Suitable agents also include compounds that inhibit stimulators of extracellular matrix production in vascular walls and compounds that otherwise reduce the amount or strength of extracellular matrix in vascular walls. Examples of mitogens targeted in accordance with the invention include growth factors, for example, insulin-like growth factor (IGF), platelet-derived growth factors, endothelial growth factors, fibroblast growth factors (FGF), transforming growth factors (TGF), thrombin and other products of the coagulation and fibrinolytic system that are mitogenic. Examples of extracellular matrix production stimulators include TGFβ, ascorbate and other growth factors, including connective tissue growth factor (CTGF).

Preferred agents suitable for use in the invention include compounds that neutralize the effect of growth factors responsible for vascular cell proliferation and/or extracellular matrix production by binding to the growth factor, or the receptor therefor, or by otherwise inhibiting the binding of the growth factor to its receptor. Antibodies (e.g., monoclonal antibodies) specific for growth factors that are involved in proliferation of cells of the vascular wall (e.g., growth factors that are elaborated from clots during the first several days following SAH) represent one type of such compounds. Such antibodies are available from a variety of sources, including Chemicon, Inc. and R&D Systems, Inc (e.g., anti-TGF-β receptor antibodies, anti PDGF-AA and -BB antibodies, anti PDGF receptor α and receptor β antibodies). Retinoids can also be used to inhibit vascular cell growth (see Chen et al, J. Clin. Invest. 102(3):653 (1998); Braunhut et al, J. Biol. Chem. 269(18):13472 (1994); Davidson et al, J. Biol. Chem. 272(1):345 (1997)).

In addition to the above, interruption of the cell cycle/cell proliferation can be effected using chemotherapeutic agents that are safe and efficacious when administered to the CSF. Chemotherapeutic agents that are given orally or intravenously but distribute into the CSF can also be used. Examples of such agents include BCNU (bis(chloroethyl)nitrosourea, which distributes into the CSF following IV administration), methotrexate (which can be admininistered IV or directly into CSF), and 5-fluorouracil (distributes into the CSF). (See also Goodman et al, eds. Goodman & Gilman's The Pharmacological Basis of Therapeutics. New York, McGraw-Hill, Health Professions Division, 1996; Gumerlock and Neuwelt, Blood-brain Barrier Modification in the Delivery of Antitumor Agents. In: Wilkins and Rengachary, eds. Neurosurgery. McGraw-Hill, N.Y. (1996), pages 1967-19071.)

Preferred agents for use in the invention also include compounds that inhibit the synthesis, secretion or strengthening (e.g., via cross-linking) of extracellular matrix, as well as compounds that weaken or degrade extracellular matrix. PH (prolyl-4-hydroxylase) can be inhibited specifically and irreversibly by peptides containing 5-oxaproline (such as benzyloxycarbonyl-Phe-Oxaproline-Gly-benzylester) and by antraacyclines (such as doxorubicin and daunorubicin). PH can also be inhibited using weaker inhibitors (such as competitive inhibitors), including derivatives of 2-oxoglutarate (e.g., coumalic acid, pyridine 2,4 dicarboxylate, pyridine 2,5 dicarboxylate, N-oxalylglycine and 3,4-dihydroxybenzoate). (See Kivirikko et al, Matrix Biology 16:357 (1998).) LO can be inhibited specifically and strongly by small molecules such as β-aminopropionontrile (BAPN), β-bromoethylamine, p-halobenzylamines, ethylenediamine and homocysteine thiolactone. Weaker inhibitors of LO (e.g. competitive inhibitors) can also be used such as hydrazine, dipyridyl, phenylhydrazine and semicarbazide. (See Kagan, Acta Tropica 77:147 (2000).) Examples of compounds that weaken or degrade extracellular matrix include matrix metalloproteinase (MMP) and serine proteases, or mimetics thereof or derivatives thereof.

Agents that are candidates for use in the present methods can be identified using a simple binding assay. For example, a test compound can be contacted with a growth factor that stimulates proliferation or extracellular matrix production (or receptor therefor) and the ability of the test compound to bind the growth factor (or receptor) determined. For example, ELISAs (enzyme-linked immunosorbant assays) can be used. Alternatively, binding assays can take the form of competitive assays in which the ability of a test compound to compete with a receptor for binding to a growth factor is determined.

A candidate compound that is identified as being capable of binding to a growth factor (or its receptor) (or otherwise inhibiting binding of a growth factor to its receptor) can then be further assayed (bio-assayed) for its ability to inhibit cell proliferation and/or extracellular matrix production. Such assays can be conducted, for example, by measuring cell proliferation and/or extracellular matrix production in vitro using segments of excised cerebral arteries exposed to the growth factor in the presence and absence (control) of the test compound. Compounds that inhibit cell proliferation and/or extracellular matrix production can be expected to be useful as active agents in the present prevention/treatment method.

Alternatively, bio-assays can be used as the primary screen, rather than subsequent to a binding assay. As indicated above, bio-assays can be carried out by bringing cells in a blood vessel wall into contact with a growth factor and the test compound to determine if cell growth and/or extracellular matrix production is inhibited in the presence of the test compound.

Assays suitable for determining whether a test compound (proteinaceous or non-proteinaceous) can degrade/weaken extracellular matrix can be carried out using, for example, the Human Type I Collagenase Activity Assay Kit provided by Chemicon International, Inc. Temecula, Calif. 92590. In accordance with the basic principle of this assay, a test compound can be incubated with collagen bound to a solid support under conditions such that degradation of the collagen can occur (when the test compound has collagen degrading activity). A determination can made as to whether degradation of the collagen occurs in the presence of the test compound (as compared to in its absence), for example, by washing the solid support following incubation with the test compound and measuring the amount of collagen that remains attached to the solid support.

Blood vessel cells are capable of producing compounds that degrade/weaken extracellular matrix, MMP-1 being one such compound. Blood vessels cultured in vitro can be exposed to a test compound and the determination made as to whether the test compound stimulates the release of a compound(s) (e.g., MMP-1) that degrades/weakens extracellular matrix. Culture medium levels of release compound (e.g., MMP-1) can be semi quantified using commercial assays such as the MMMP-1 Immunoassy Kit provided by Chemicon International, Inc.

Agents of the invention, including those identifiable using one or more of the above-described assays, can be formulated into pharmaceutical compositions with a suitable carrier and at a strength effective for administration by various means to a patient. Pharmaceutical compositions that contain agents of the invention can be prepared using standard techniques. Such compositions can be prepared in dosage unit form and as oral consumables or injectables, either as liquid solutions or suspensions, however, solid forms suitable for solution in, or suspension in, liquid prior to injection can also be prepared. The preparation can also be emulsified. The agent can be mixed with excipients that are pharmaceutically acceptable. Suitable excipients include water, saline, dextrose, glycerol, or the like, and combinations thereof. In addition, if desired, the composition can contain minor amounts of auxiliary substances such as wetting or emulsifying agents, and pH buffers that enhance the effectiveness of the agent. Where appropriate, the composition can be sterile.

The compositions of the invention can be administered in a manner compatible with the dosage formulation, and in a therapeutically effective amount. The quantity to be administered depends on the patient, the agent and the effect sought. Suitable regimes can be readily determined by one skilled in the art.

A variety of administrative techniques can be used, depending on the agent, including oral administration, parenteral techniques such as subcutaneous, intravenous, intramuscular and intraperitoneal injections, catheterizations and the like. In the case of antibodies, administration is preferably through a catheter placed into the subarachnoid space (Mapstone et al, Techniques of Ventricular Puncture. In: Wilkins and Rengachary, eds. Neurosurgery, McGraw-Hill, N.Y. (1996), pages 179-183). This technique can be used with other agents of the invention. Antibodies (as well as other agents of the invention) can also be injected through a needle placed in the cerebrospinal fluid in the lumbar spine using a "single-shot" technique (Gaiser, Spinal, Epidural and Caudal Anesthesia. In: Longnecker and Murphy (eds) Introduction to Anesthesia, W B Saunders Co., Philadelphia, 1997; Miller, ed., Anesthesia, Churchill Livingstone, Inc., New York). A potential advantage of catheter-based administration of agents with relatively short half lives is that doses can be given at frequent (e.g., daily) intervals, allowing for re-dosing and continued efficacy. Alternatively, delivery of the agents of the invention to the CSF can be accomplished using an Ommaya reservoir such as described by Collins (J. Neuro-Onc. 1:283 (1983)), Sandberg et al (Neurosurgery 47:49 (2000)) and Laske et al (Neurosurgery 41:1039 (1997)).

Certain aspects of the invention are described in greater detail in the non-limiting Examples that follow.

EXAMPLE I

Growth Factor Levels in Human Cerebrospinal Fluid (CSF) of SAH Patients

Methods—CSF Samples

CSF was collected from lumbar or ventricular drainage devices from patients suffering from subarachnoid hemorrhage (SAH patients, n=14), 2 patients from cerebral contusion, 2 from unruptured cerebral aneurysm, 1 from obstructive hydrocephalus, and 1 from intracerebral hemorrhage (Non-SAH Patients, n=6). The average patient age was 56, and ranged from 16 to 86 years. The patients were 13 women and 7 men; 14 Caucasian and 6 African-American. Control samples were obtained from normal healthy volunteers undergoing atraumatic lumbar puncture in a separate IRB approved study (Normal Controls, n=8).

CSF samples were collected from the drainage apparatus by sterile sampling technique. The deadspace volume from the drain tubing was discarded prior to collecting 1-6 mL of fresh CSF in a polystyrene centrifuge tube. CSF samples were centrifuged at 270×g for 15-30 min. at room temperature (Centra CL2 centrifuge, International Equipment Co., Needham Heights, Mass.) to remove red blood cells, non-activated platelets, and other cellular debris. The supernatant was then frozen at −80° C. for later analysis.

Methods—Enzyme-Linked Immunosorbent Assays (ELISAs)

CSF Samples were thawed from −80° C. to room temperature and then assayed in duplicate for the presence of basic fibroblastic growth factor (b-FGF), platelet-derived growth factor-AB (PDGF-AB), and vascular endothelial growth factor (VEGF). ELISA assays were conducted according to manufacturer's instructions (R&D Systems Inc., Minneapolis, Minn.). ELISA data were analyzed by the Student's test for comparisons between subgroups within the data set.

Results

Growth factor levels in CSF of SAH patients were significantly higher than controls for PDGF-AB and VEGF, both during the first week after SAH, and for all time points measured (Table 1). For patients with neurologic injury that did not have SAH, growth factor levels were intermediate between SAH patients and controls.

TABLE 1

Peak growth factor levels in CSF. Growth factor levels in CSF of SAH patients were significantly higher than controls for PDGF-AB and VEGF, both during the first week after SAH, and for all time points measured (Table 1). For patients with neurologic injury that did not have SAH, growth factor levels were intermediate between SAH patients and controls.

| Group | n | Peak PDGF-AB (pg/mL) | Peak VEGF (pg/mL) |
|---|---|---|---|
| SAB Patients - all time points | 12 | 186 ± 177 *** | 73 ± 93 *** |
| SAH Patients - first 7 days | 10 | 264 ± 211 ** | 91 ± 116 * |
| Non-SAH Patients | 6 | 81 ± 94 | 19 ± 22 |
| Normal Controls | 8 | 18 ± 6 | 13 ± 9 |

Values are means ± standard deviations.

TABLE 1-continued

Peak growth factor levels in CSF. Growth factor
levels in CSF of SAH patients were significantly higher
than controls for PDGF-AB and VEGF, both during the first
week after SAH, and for all time points measured (Table 1).
For patients with neurologic injury that did not have SAH,
growth factor levels were intermediate between SAH patients
and controls.

| Group | n | Peak PDGF-AB (pg/mL) | Peak VEGF (pg/mL) |
|---|---|---|---|

\*\*\* $P < 0.001$ for difference with Normal Controls.
\*\* $P < 0.005$ for difference with Normal Controls.
\* $P < 0.02$ for difference with Normal Controls.

PDGF-AB and VEGF levels in the CSF of SAH patients showed high concentrations during the first several days, followed by a gradual decay (FIG. 1A, B). PDGF-AB and VEGF levels began to approach control levels 3 weeks after SAH. In contrast, b-FGF, a growth factor that is not secreted by activated platelets and hence served as a negative control, was not substantially elevated in SAH or non-SAH patients (SAH patients: 3.9±10.2 pg/mL; Non-SAH patients: 3.5±3.8 pg/mL; Normal Controls: 0±0.1 pg/mL; FIG. 1C).

The amount of scatter in PDGF-AB and VEGF levels may be partially due to the vagaries of sampling: in many cases, CSF samples were obtained from ventriculostomy drains. Sampling is thus subject to two major diluting factors: (1) lateral ventricles reside upstream in CSF flow from the possible sources of subarachnoid clot on the cerebroarterial circle (Circle of Willis); (2) the subarachnoid clot (eg, ~20 mL) is approximately one tenth of the CSF volume, ~200 mL.

To examine whether CSF growth factor levels correlated with subarachnoid blood volume, levels in Fisher grade 3 and 4 patients were compared. CSF VEGF levels were significantly greater in Fisher grade 4 patients as compared in to grade 3 (Table 2). CSF PDGF-AB levels, though greater in grade 4 patients, did not reach statistical significance. 12 of 14 patients with SAH had CSF samples drawn within 48 hours of symptoms onset. 6 of 11 patients developed clinical and/or arteriographic vasospasm (one patient It was equivocal). Neither PDGF-AB nor VEGF were significantly different between groups of patients with vasospasm or without.

TABLE 2

Growth factors in CSF up to 48 hours and SAH.
CSF VEGF levels were significantly greater in Fisher grade
4 patients as compared in to grade 3. CSF PDGF-AB levels,
though greater in grade 4 patients, did not reach
statistical significance. 12 of 14 patients with SAH had
CSF samples drawn within 48 hours of onset of symptoms. 6
of 11 patients developed clinical and/or arteriographic
vasospasm (one patient was equivocal). Neither PDGF-AB nor
VEGF were significantly different between groups of
patients with vasospasm or without.

| Growth Factor | Fisher Grade {Fisher, 1980} | | Clinical Evidence of Vasospasm | |
|---|---|---|---|---|
| | Grade 3 (n = 3) | Grade 4 (n = 9) | No (n = 5) | Yes (n = 6) |
| PDGF-AB (pg/mL) | 135 ± 49 | 391 ± 246 | 403 ± 335 | 254 ± 158 |
| VEGF (pg/mL) | 6 ± 9 | 125 ± 140* | 132 ± 173 | 72 ± 107 |

Values are means ± standard deviations.
\*$P < 0.03$ for difference with Fisher Grade 3.

Thus, vascular mitogens (PDGF, VEGF) are elevated in the CSF of patients undergoing SAH, and this knowledge could lead to an improved understanding and prevention of cerebral vasospasm as a complication following SAH.

EXAMPLE II

Vascular Cell Proliferation in a Murine Model of SAH

Methods—Animal Surgery

C57/B16 male mice were fasted for 12 hours to control for glucose levels. Anesthesia was induced with a mixture of 5% halothane and 50% $N_2$/50% $O_2$. Mice were intubated and mechanically ventilated (Harvard Rodent Ventilator). Anesthesia was maintained with a mixture of 0.5-1.5% halothane and 50% $N_2$/50% $O_2$. Temperature was kept at 37° C. using a heating lamp and a pericranial needle electrode thermostat. Arterial blood gasses were monitored prior to the insult, and $O_2$ saturation (>95%) and $PCO_2$ (35-50 mmHg) were kept within pre-established ranges prior to the insult. Blood pressure was monitored and kept ≧60/40 mmHg by adjusting the halothane concentration.

The right external carotid artery (ECA) and right common carotid artery (CCA) were exposed through a midline ventral approach. The ECA was ligated and a 5-0 blunted monofilament was introduced into the proximal stump through a small incision. To induce an endovascular injury, the monofilament was used to puncture the proximal segment of the anterior cerebral artery (ACA). The suture was advanced 5 mm further than the resistance point (proximal ACA) to perforate the artery. Sham operated mice underwent identical procedures, except that the suture was not advanced 5 mm to perforate the ACA. The suture was immediately withdrawn to allow reperfusion and SAH in the right ventral anterior quadrant of the brain. The same surgeon performed all operations. Following surgery, animals were supported until brain harvesting, and then were humanely sacrificed. This study involved sham (n=9) and SAH (n=9) animals, each divided into 3 h, 24 h, and 72 h brain harvesting time points (n=3 each)

Methods—Brain Harvesting

In anesthetized animals, a median upper abdominal incision was used to enter into the abdominal and thoracic cavities. A 23-gauge needle connected to 3.2 mm internal diameter plastic tubing (Tygon) was inserted bluntly into the left ventricle cannalizing the ascending aorta. At the ascending aorta, the catheter tip was secured with an aneurysmal microclip. Approximately 20 mL of normal saline were injected at a pressure of 60 to 80 mmHg. Thereafter, the euthanized animals were perfused with 4% paraformaldehyde solution in PBS for 10 minutes using the same perfusion pressure. Cadavers were kept refrigerated at 4° C. for 3 hours, and then brains were harvested and placed in 70% alcohol, dehydrated, and paraffin embedded.

Methods—Immunostaining

5 μm coronal brain sections were deparaffinized and then immunostained for the presence of proliferating cell nuclear antigen (PCNA; DAKO) (Niklason et al, Science 284:489-(1999)), with methyl green counterstain. PCNA-positive nuclei were quantified by two blinded, independent observers on 4 sections from each brain, counting only ACA-localized positive nuclei, then averaged for each brain. Sham-operated and SAH animals were compared for positive nuclei using Student's t-test. For PDGF stains, a primary anti-PDGF-B chain antibody (Chemical International, Temecula, Calif.) was used in combination with the Vectastain ABC peroxidase kit, per manufacturer's instructions.

Results

Figure 2:
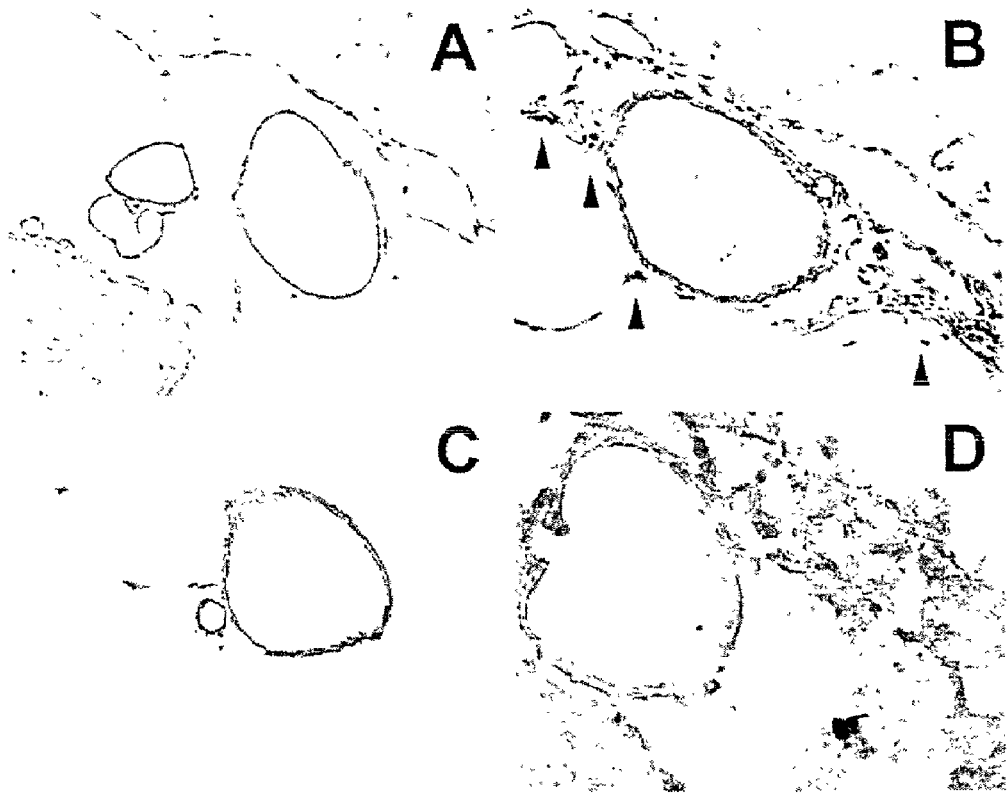
FIGS. 2A-2D.
Figure 3:
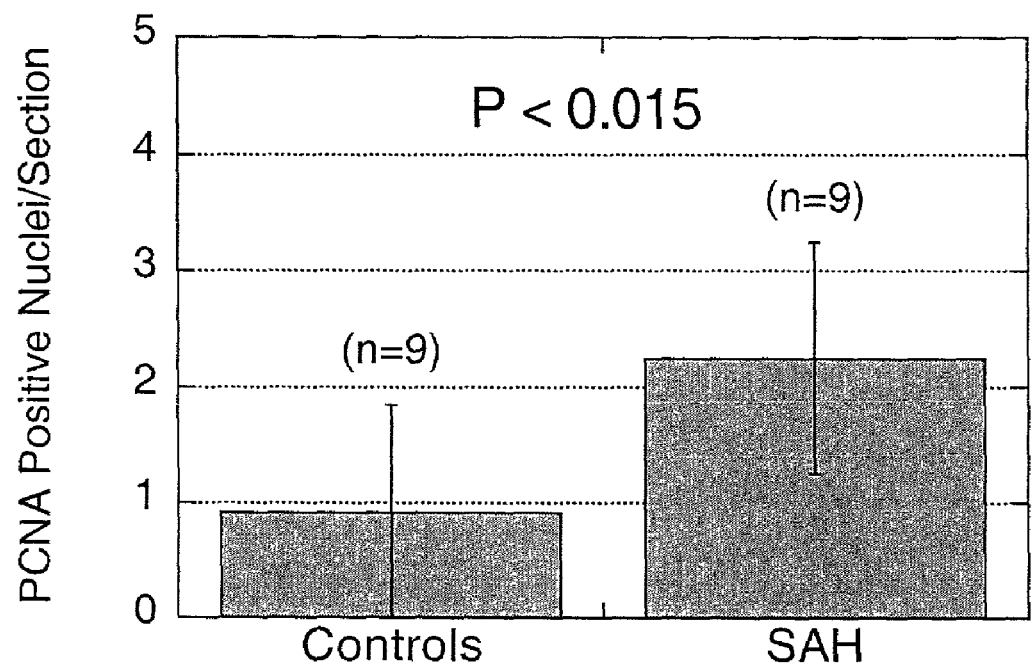
FIG. 3. Summary of immunostaining for proliferating cell nuclear antigen (PCNA) in sham-treated and SAH mice. More smooth muscle cell replication was seen in SAH animals, and this difference reached statistical significance when all time points (3, 24, and 72 h) were considered (P<0.015).

Immunochemical staining of murine brains revealed clear differences between SAH and sham-operated animals (FIG. 2A, B). Staining for PCNA, a nuclear cyclin involved in DNA replication, revealed marked increases in perivascular proliferation after SAH at all time points examined. While many PCNA-positive smooth muscle cell nuclei were noted within vascular media of the ACA and other cerebral arteries, the majority of positive nuclei were fibroblasts located in the adventitia and connective tissue surrounding cerebral vessels (arrowheads, FIG. 2B). More smooth muscle cell replication was seen in SAH animals, and this difference reached statistical significance when all time points were considered ($P<0.01$; FIG. 3).

PDGF-B immunostaining, which reveals both PDGF-AB, the major constituent of platelet α-granules, and PDGF-BB, indicated that there is extensive protein deposition of PDGF in the areas of thrombus formation in this SAH model (FIG. 2C, D). PDGF staining was essentially absent in control specimens.

Extensive smooth muscle and fibroblast proliferation was observed following SAH, and this cellular replication correlates with evidence of PDGF —vascular cell mitogen - near the sites of injury. Therefore, inhibition of PDGF might attenuate perivascular cell proliferation observed in SAH and thus ameliorate the progression of cerebral vasospasm.

EXAMPLE III

An In Vitro Human Model of SAH

Methods—Human Pial Arteries

To collect segments of pial cerebral arteries, patients who were undergoing temporal lobectomy for intractable seizures were enrolled in an IRB-approved study. During the lobectomy procedure, normal segments of pial artery overlying the resected brain parenchyma (3-4 mm lengths of artery, otherwise discarded) were dissected free from underlying brain tissue. Segments were stored immediately in culture medium at 37° C. To obtain fresh human blood for culture with human pial arteries in vitro, 5 mL samples of venous blood were collected from a single volunteer, with IRB approval.

Methods—In Vitro Model of SAH in Human Pial Arteries

Vessel samples from three patients were each divided into four 1mm length segments. The first segment was a "time zero" specimen that served as an initial control (group 1). This specimen was formalin fixed within one hour of tissue harvest. The three remaining segments were cultured for 7 d: (a) in growth medium, with no blood contact (group 2); (b) in growth medium, and in contact with 200 μL freshly-clotted human blood (group 3); and (c) in growth medium, in contact with 200 μL freshly-clotted human blood pre-mixed with inhibitory antibodies to PDGF-AB and PDGF-BB (group 4). For pial vessel culture, growth medium consisted of Dulbecco's Modified Eagles Medium (DMEM) with human serum (0.25%), ascorbic acid (50 μg/mL), copper sulfate (3 ng/mL), proline (50 μg/mL), glycine (50 μg/mL), alanine (20 μg/mL), 4-(2-Hydroxyethyl)-l-piperazineethanesulfonic acid (HEPES; 10 mM). All reagents were obtained from Sigma (St. Louis, Mo.) unless noted otherwise. The serum percentage (0.25%) was selected to result in PDGF-AB levels in growth medium of 580 pg/ml, which is in the range of values measured in CSF of SAH patients.

For culture experiments, artery segments were placed on the top of inserts of 6-well tissue culture plates (Transwell, Corning Costar Corp., Cambridge, MA). For group 2, the well was filled with 13 mL of growth medium. For groups 3 and 4, 200 μL of human blood, with or without inhibitory antibodies was allowed to coagulate on top of the segments for one hour before the wells were filled with growth medium. For group 4, anti-PDGF-AB was used at 3.8 μg/mL, (10-fold increase over the $ND_{50}$; AB1486P, Chemicon) and anti-PDGF-BB was used at 6.3 μg/mL (300-fold increase over the ND50; AB1487P, Chemicon). The levels of inhibitory antibodies required to block action of targeted growth factors were determined from direct assay of PDGF levels in the human volunteer's serum.

Medium was refreshed every 3-4 d, and after 7 d, segments were harvested, formalin-fixed, and embedded in paraffin. To assess for cellular proliferation in the vessel walls, axial sections (5 μm) were immunostained for PCNA as described in EXAMPLE II.

Results

Figure 4:
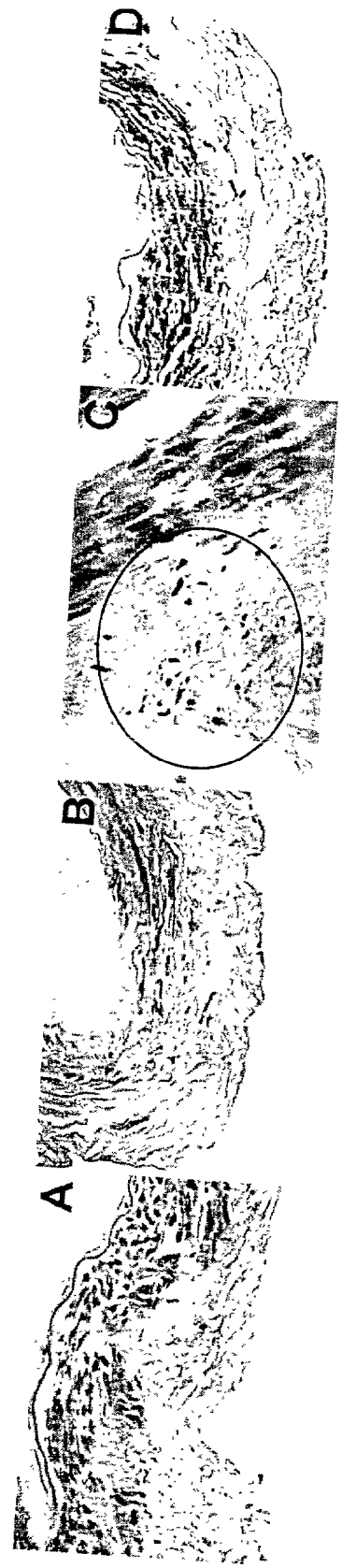
FIGS. 4A-4D.

The incidence of cellular proliferation in combination with thrombus exposure was examined in vessel segments cultured in vitro. PCNA staining revealed low levels of cellular replication in time-zero control segments (group 1; FIG. 4A). Vessel segments that had been cultured in growth medium alone for 7 days (group 2) served as a culture control, and these segments also showed low levels of vessel wall cellular proliferation (FIG. 4B). In contrast, segments exposed to coagulated human blood (group 3) displayed highly proliferative areas in the vessel wall, occurring most frequently in the adventitia (circled area, FIG. 4C). This proliferation appeared to be blocked by premixing the human blood prior to coagulation with inhibiting concentrations of anti-PDGF-AB and anti-PDGF-BB antibodies (Group 4; FIG. 4D).

These results strongly suggest that localized thrombus can stimulate vessel wall proliferation in cerebral arteries, and that anti-proliferative agents may be able to halt this thrombus-associated, SAH-analogous, proliferation. These results are consistent with data obtained from the murine SAH model (see EXAMPLE II), and show that this phenomenon may be generalizable across species.

All documents cited above are hereby incorporated in their entirety by reference.

What is claimed is:

1. A method of treating cerebral vasospasm that follows subarachnoid hemorrhage (SAH) comprising administering to a patient in need of such treatment an amount of an agent that inhibits vascular cell proliferation sufficient to effect said treatment, wherein said agent is a chemotherapeutic agent.

2. The method according to claim 1, wherein said chemotherapeutic agent is bis(chloroethyl)nitrosourea, methotrexate or 5-flurouracil.

* * * * *